United States Patent
Fanning et al.

(10) Patent No.: US 9,162,326 B2
(45) Date of Patent: Oct. 20, 2015

(54) INCUBATION SYSTEM WITH LOW TEMPERATURE ENCLOSURE

(71) Applicant: BIOMERIEUX, INC., Durham, NC (US)

(72) Inventors: Mark J. Fanning, Florissant, MO (US); Jacky Yam, St. Louis, MO (US); David M. Robbins, Lake Saint Louis, MO (US); Kevin G. Ketsenburg, O'Fallon, MO (US); James C. Bishop, Columbia, MO (US)

(73) Assignee: bioMerieux, Inc., Durham, NC (US)

( * ) Notice: Subject to any disclaimer, the term of this patent is extended or adjusted under 35 U.S.C. 154(b) by 76 days.

(21) Appl. No.: 13/803,677

(22) Filed: Mar. 14, 2013

(65) Prior Publication Data

US 2013/0192036 A1    Aug. 1, 2013

Related U.S. Application Data

(62) Division of application No. 12/283,191, filed on Sep. 9, 2008, now Pat. No. 8,420,383.

(51) Int. Cl.
  *C12M 1/00* (2006.01)
  *C12M 3/00* (2006.01)
  *C12M 1/34* (2006.01)
  *B23P 6/00* (2006.01)

(52) U.S. Cl.
  CPC *B23P 6/00* (2013.01); *C12M 41/14* (2013.01); *Y10T 29/49716* (2015.01)

(58) Field of Classification Search
  CPC ...... C12M 21/00; C12M 23/48; C12M 41/00; C12M 41/12; C12M 41/14; C12M 41/34
  See application file for complete search history.

(56) References Cited

U.S. PATENT DOCUMENTS

| 4,701,415 | A | * | 10/1987 | Dutton et al. | 435/286.6 |
| 5,601,143 | A | * | 2/1997 | Binder | 165/61 |
| 6,180,397 | B1 | * | 1/2001 | Binder | 435/303.1 |
| 6,503,751 | B2 | * | 1/2003 | Hugh | 435/303.1 |
| 7,838,286 | B2 | * | 11/2010 | Tamaoki et al. | 435/303.1 |

FOREIGN PATENT DOCUMENTS

| JP | 07-334250 | * | 12/1995 |
| JP | 2006-061126 | * | 3/2006 |

* cited by examiner

*Primary Examiner* — Nathan Bowers (57) ABSTRACT

An incubator is fitted with an enclosure which surrounds the incubator. A cold air generation system supplies relatively cold air to a space formed between enclosure and the incubator. The system supplying the cold air can be embodied in a cart or base upon which the incubator sits. The enclosure is also placed on the base in a manner such that it substantially envelops the incubator. The top of the cart has openings for egress of cold air and return of air so that air may circulate in a closed loop. The incubator, cold air supply system and enclosure present a solution for incubating samples in a nominal 20-25° C. temperature environment. The enclosure, which is preferably insulated, may include a void or opening which exposes doors or other access device of the incubator, allowing direct access to the samples in the incubator while the rest of the incubator is enveloped by the enclosure.

5 Claims, 8 Drawing Sheets

INCUBATION SYSTEM WITH LOW TEMPERATURE ENCLOSURE

CROSS REFERENCE TO RELATED APPLICATIONS

The present application is a divisional of U.S. patent application Ser. No. 12/283,191, filed Sep. 9, 2008. The entire disclosure content of this application is herewith incorporated by reference into the present application.

FIELD OF THE INVENTION

This invention relates to the field of incubators, and more particularly to an incubator that is designed to maintain an incubation temperature that is close to room temperature, e.g., between 20 and 25° C.

BACKGROUND

Figure 1:
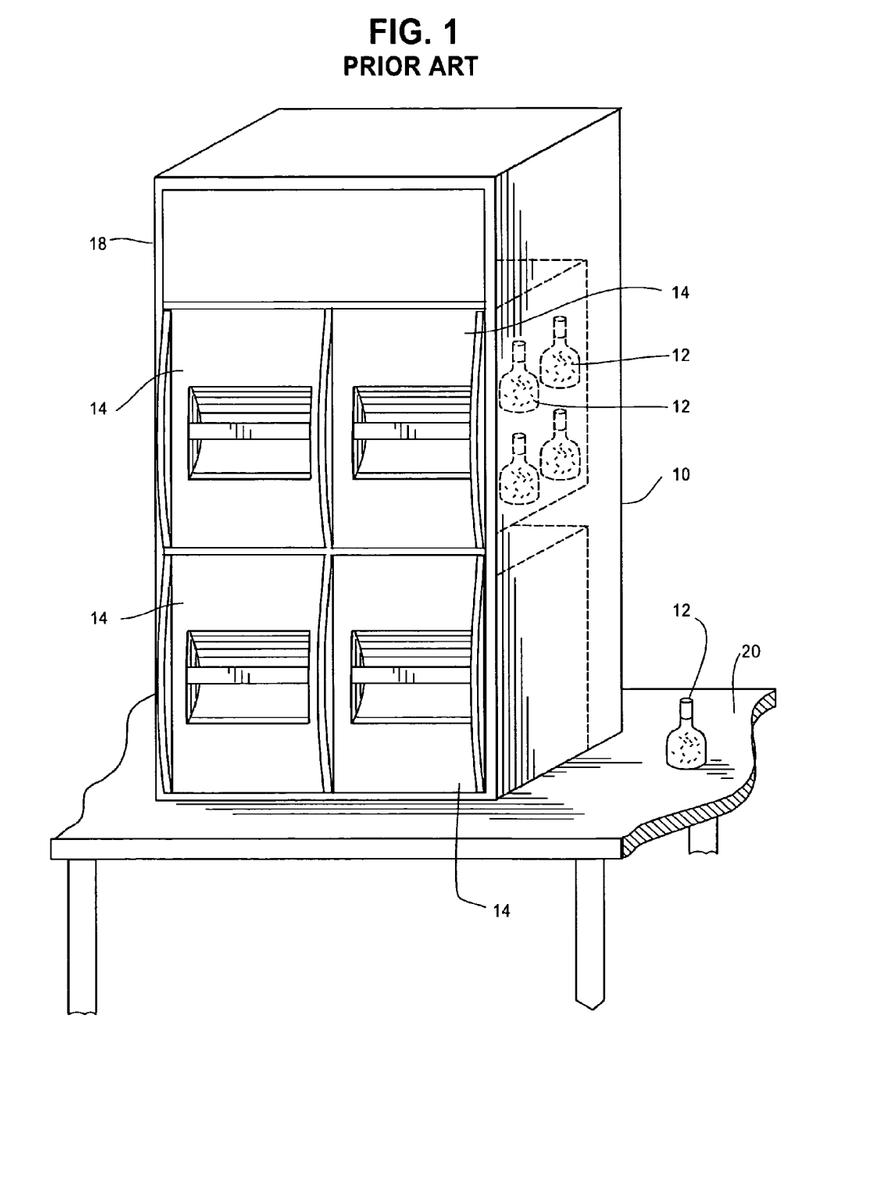
FIG. 1 is an illustration of a prior art incubator designed to incubate blood collection bottles, which is shown placed in a laboratory on the lab bench.

Incubators for incubating biological samples, such as human blood samples placed in a bottle or like container, are known in the art. FIG. 1 shows one such incubator 10, marketed by the applicants' assignee bioMérieux, Inc. as the BacT/Alert 3D ™ incubation system. The incubator 10 is designed to incubate blood collection bottles 12 which contain a culture medium. The incubator has drawers 14 which pull out from the rest of the incubator to allow the user to insert and remove the bottles 12 from the incubator 10.

The incubator further includes optical sensors (not shown) which read the bottles 12 to determine whether a reaction has occurred between the sample in the bottles and a growth medium in the bottle. The sensors and their method of operation are described in the patent literature, see U.S. Pat. No. 5,164,796. The incubator has an electronics unit 18 positioned at the top of the incubator which receives signals from the optical sensors and which regulates the heater system (not shown) of the incubator which in turn regulates the internal temperature of the incubator. The incubator 10 is typically installed in a biological testing laboratory, e.g., located in a hospital, clinic or other site, and placed on the laboratory bench 20.

In the microbiology testing industry, there are generally two distinct market segments: biopharma and food. These two segments have unique microbiological testing and incubation needs. In particular, the biopharma segment closely follows worldwide Pharmacopoeia methods, which includes microbiological testing and incubation of samples at two temperature ranges: 30-35° C. and 20-25° C. In comparison, the food and other clinical users primarily set their incubators at 36 or 37° C.

The current BacT/ALERT 3D incubator 10 of FIG. 1 is designed to perform at an incubation temperature of 7° C. above ambient to 45° C. When placed in a normal lab environment (ambient temperature approximately 20-22° C.), the temperature differential is sufficiently large that the incubator can reliably incubate within the 30-35° C. incubation range. However, under normal laboratory working conditions in which the laboratory and incubator is maintained in a room temperature (20-22° C.) ambient environment, some incubators are not capable of maintaining a stable incubation range of 20-25° C. Simply leaving the specimen to be incubated out on the laboratory bench at "room temperature" is of course not acceptable, as the environment is not reliably temperature controlled (e.g., a window may be left open, the air conditioning system may not work properly, the heating system may be turned down at night or over the weekend to save energy, etc.).

In order for some incubators to work properly and maintain the 20-25° C. (nominal 22.5° C.) incubation range, in the past the entire incubator is moved to a walk-in environmental chamber which maintains an ambient environment of approximately 13° C. or less. However, this approach does not provide an efficient work environment, because the walk-in environmental chamber is typically not conveniently located, e.g., it is down the hall or on another floor. Moreover, many larger facilities have many incubators such as the incubator 10 of FIG. 1. The walk-in environmental chamber is typically in a separate location away from the other incubators, thus making use of the incubators in the environmental chamber more inconvenient and inefficient.

An alternative approach that has been considered is to cool the entire laboratory space where the incubators are located down to say 10-13 degrees C. However, this is not a comfortable work environment for laboratory technicians, as they have to bundle up to stay warm and contend with working with cold hands.

Organon Teknika, the company which originally designed the incubator module 10 shown in FIG. 1, at one time developed an incubation instrument known as the "Kool Boy" to satisfy the need for incubation at cooler temperature than 30° C. The design included a cooling unit placed in a custom cart with an incubator on top. The cooling unit was a window air conditioner. The air was drawn in from the front of the cart and the cool air exited out duct work along the back edge of the cart. The incubator rear panel was removed and replaced with duct work that attached to the top rear of the cart. The cool air from the cooling unit blew directly into the incubator. Firmware within the incubator controlled the temperature of the airflow. This unit was considered to be too noisy for the laboratory environment due to the high blower RPMs. The 220 VAC power supply the unit required was not easily adaptable to most laboratories either. The product was a commercial failure for these and other reasons, and supposedly only 1 or 2 instruments were ever sold.

The incubation system and apparatus of this invention solves this problem of providing incubators which can properly and reliably maintain an incubation temperature at or near room temperature (20-25° C.), while allowing laboratory workers to work in a normal laboratory environment at room temperature and allow all the incubators to be maintained in the same vicinity by avoiding the use of special environmental chambers and resulting inefficiencies. This invention also overcomes the many deficiencies that the Kool Boy instrument suffered from.

SUMMARY

In a first aspect, an incubation system is disclosed. The system is designed for incubating samples, such as biological samples, agar plates streaked with a bacterial culture, blood collection bottles, etc. in a controlled temperature environment. This temperature environment is preferably but not necessarily approximately room temperature, such as between 20 and 25° C. The nature of the sample or the device containing the sample to be incubated is not important. The example of blood collection bottles herein is offered only by way of explanation and not limitation.

The system includes an incubator having an exterior and an interior and one or more access features on the exterior providing access to the interior of the incubator for loading sample containers into the incubator and removing the sample containers. The access features may take the form of doors, drawers or other format. The incubator includes a heating system for maintaining the temperature of the interior of the incubator at a nominal desired temperature, e.g., 22.5° C.

The system includes a machine (refrigeration unit) for generating a supply of cold air. The machine is preferably incorporated into a cart or base structure upon which the incubator sits. The temperature of the air produced by the refrigeration unit is typically below the temperature of the incubator, such as 10° C.

The system further includes an enclosure external from and substantially enveloping the incubator. The enclosure is configured and constructed so as to define a space or region to exist between the exterior of the incubator and the enclosure. This space or region between the enclosure and the incubator receives cold air from the machine generating the supply of cold air. Thus, relatively cool air is provided to the exterior of the incubator. The enclosure in preferred embodiments is insulated, e.g., made of an insulative material or made from a non-insulative material (sheet metal) and insulated such as foam added to the material. The enclosure is sized and shaped so as to substantially surround the exterior of the incubator in order to maintain an ambient environment on the exterior of the incubator. The enclosure provides an ambient environment for the incubator which is sufficiently cooler from the nominal temperature of the incubator such that the incubator can reliably incubate at a temperature in the 20-25° C. range, thereby allowing the incubation system to be placed in a room temperature environment.

In a preferred embodiment, the enclosure includes a void or opening exposing the one or more access features on the exterior of the incubator, wherein a user may directly access the contents stored in the incubator while the rest of the incubator is substantially enveloped by the enclosure. It is also possible to provide an enclosure that completely envelops the incubator but which has an access feature such as a door to allow the user to gain access to the incubator drawers or doors and thus the sample containers inside the incubator.

In one configuration, the machine supplying cold air is incorporated into a base, which may take the form of a cart or like device which may or may not be mobile (i.e., have wheels). The insulated enclosure and incubator are placed on the base. In one configuration, the base and the insulated enclosure are constructed and arranged as a retrofit assembly for a pre-existing incubator, and shipped as a kit to the site of the incubator. The base includes a first opening for egress of cold air from the base and a second opening for return of air from region between the enclosure and the incubator, whereby air is circulated in a closed loop from the base, to the space between the enclosure and the incubator, and back to the base.

In a preferred configuration, the enclosure includes seals making a substantially air-tight seal between the enclosure and the base and between the enclosure and the incubator in the area surrounding the void in the enclosure. The seals prevent introduction of ambient air into the region between the enclosure and the incubator. This design allows for closed loop circulation of cool air to and from the incubation enclosure and minimizes formation of condensation inside the incubation enclosure.

In another possible configuration, the incubator includes a top portion and an electronics module positioned in the top portion of the incubator. The insulated enclosure is constructed and arranged into a first or lower compartment surrounding the incubator and a second or upper compartment surrounding the top portion of the incubator. The two compartments are separated from each other (e.g., using baffles), such that air from the system supplying cold air does not enter the upper compartment. This design prevents any possible damage to the electronics due to condensation as the cool air is not circulated to the upper compartment.

In another aspect, an incubation apparatus is provided comprising, in combination: (a) an incubator, the incubator having an exterior and an interior and one or more access features on the exterior providing access to the interior of the incubator, the incubator further comprising a source of heat for maintaining the interior of the incubator at a nominal temperature; and (b) an insulated enclosure enveloping the incubator, the enclosure having an interior region receiving cold air from a source, wherein the insulated enclosure is sized and shaped so as to substantially surround the exterior of the incubator, the interior region defining a region wherein air from the source at a temperature below the nominal temperature may circulate over the exterior of the incubator.

In one possible configuration, the incubator incubates sample containers containing samples collected from human patients. Preferably, the incubator further includes a sensor for obtaining sensor readings from the sample containers.

In another aspect, the present invention may take the form of a cool chamber apparatus for installation around an incubator. The incubator has a front side having one or more access feature of obtaining access to the interior of the incubator. The cool chamber apparatus includes an insulated enclosure sized and shaped so as to substantially envelop the incubator and has a top panel and first, second and third side panels for covering the first, second and third side panels of the incubator and fourth side having an void or opening exposing the access features of the incubator.

In still another aspect, we have invented a method of modifying an incubator, comprising the steps of:

a) obtaining a retrofit kit, comprising (a) a base containing a source of cold air and (b) an enclosure, preferably but not necessarily insulated, at a site where the incubator is located, the base having a first opening for egress of cold air and a second opening for return of air to the base;

b) placing the incubator on the base;

c) placing the enclosure on the base in a manner such that the enclosure surrounds the incubator and the first and second openings in the base are peripheral to the incubator but internal to the enclosure such that cold air may circulate on the exterior of the incubator and return to the base in a closed loop.

In a preferred configuration embodiment, the enclosure includes a void exposing an access feature of the incubator enabling direct access to the contents of the incubator while the incubator is substantially enveloped by the enclosure. Alternatively, the enclosure can completely envelop the incubator and the enclosure includes a strategically placed or like access feature permitting access to the door or drawers of the incubator.

DETAILED DESCRIPTION

Overview

Figure 2:
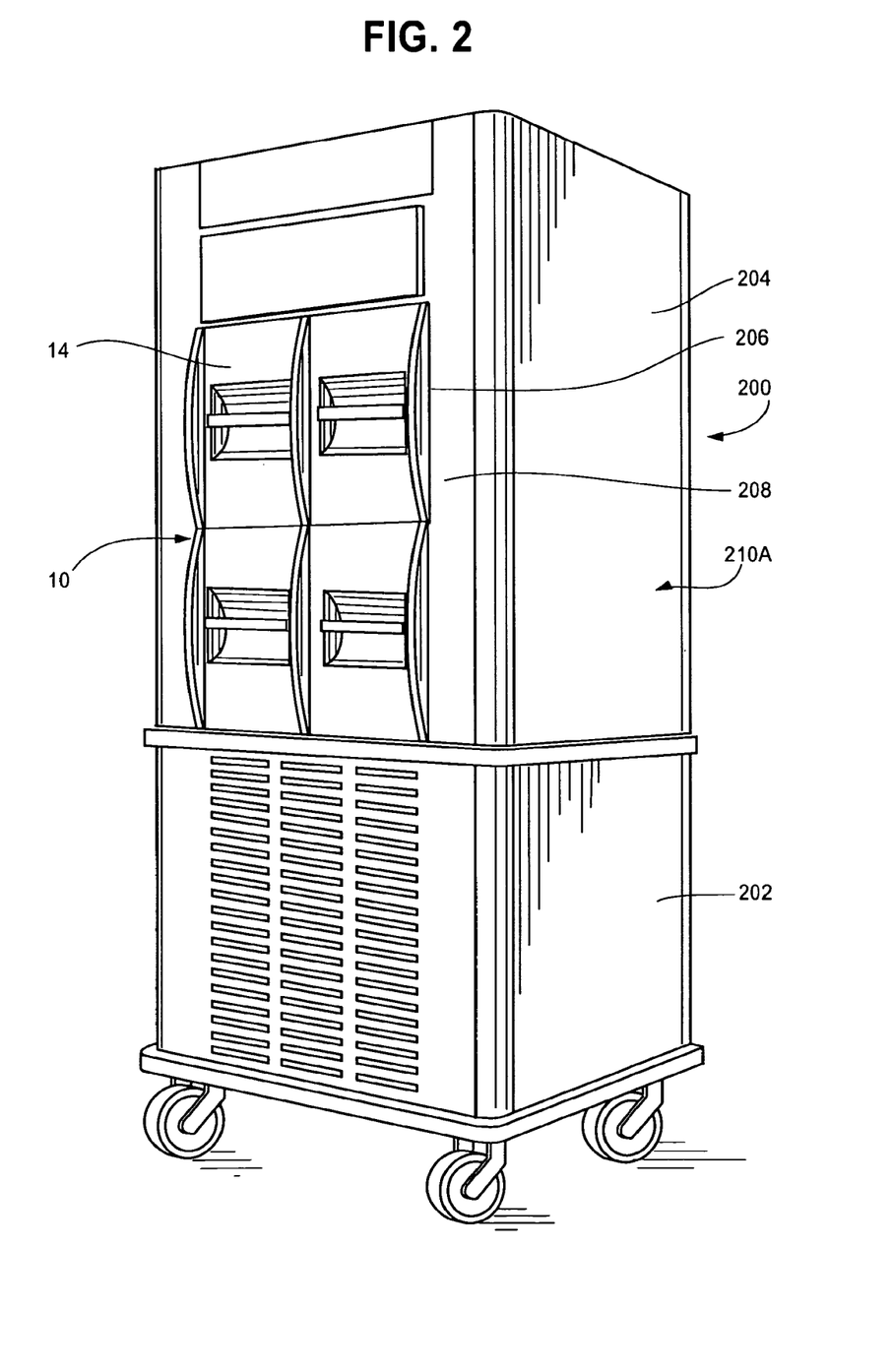
FIG. 2 is a perspective view of an incubation system according to one embodiment of this invention. The system includes an incubator (such as for example the incubator of FIG. 1), a base containing a machine generating cold air, and an enclosure (typically but not necessarily insulated or made from an material having intrinsic insulation properties) surrounding the incubator. The enclosure includes a void (opening in the front wall of the incubator) which exposes the drawers of the incubator and allows direct access to the contents of the incubator.

Referring now to the Figures, FIG. 2 is a perspective view of an incubation system 200 according to one embodiment of this invention. The system 200 includes an incubator 10 (such as for example the incubator of FIG. 1), a base or cart 202 containing a machine generating a supply of cold air, and an enclosure 204 surrounding the incubator 10. The enclosure 204 is typically, but not necessarily, insulated. That is, the enclosure has insulation added to the shell or skin forming the enclosure 204 and/or the enclosure 204 is made from a material and/or thickness such that it has intrinsic insulation properties without addition of extra insulation.

The incubator 10 and enclosure 204 are placed on the top of the base 202. The base 202 serves as a mobile base for the enclosure 204 and incubator 10 to sit on, while also housing a refrigeration machine 700 (shown in FIG. 7) generating cold air, and the power supply for the refrigeration machine. The power supply adjusts the input voltage from most world wide power sources to provide power to the refrigeration unit. In the illustrated embodiment, the refrigeration machine 700 (FIG. 7) in the base 202 produces a 10° C. airflow. This temperature setting is offered by way of example only and may vary depending on the nominal temperature maintained by the incubator, the amount of insulation present in the enclosure 204, the ambient temperature environment, and whether the system uses a feedback temperature control system including a temperature sensor for the enclosure, described below.

The incubator 10 includes a heating system (conventional, not shown) which provides the nominal temperature incubation environment for the bottles 12 of FIG. 1 contained within the incubator. This temperature in the illustrated embodiment is in the range of 20-25° C., such as 22.5° C.

The enclosure 202 in the preferred embodiment is an insulated cabinet that substantially surrounds and envelops the incubator 10 and thus provides a relatively cool ambient environment for the incubator 10 to work in. Preferred embodiments provide for the void or opening 206 in the front wall 208 of the enclosure 204 to give the lab technician direct access to the drawers 14 of the incubator 10.

Figure 6:
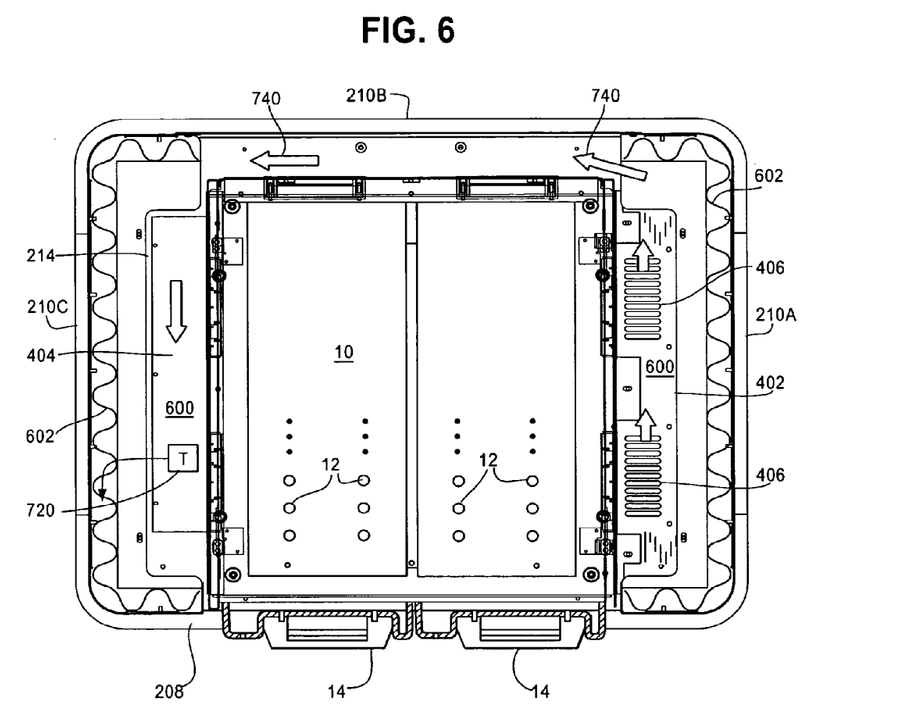
FIG. 6 is a cross-sectional view of the incubation system of FIGS. 2, 3 and 5 taken long the lines 6-6 of FIG. 3.
Figure 7:
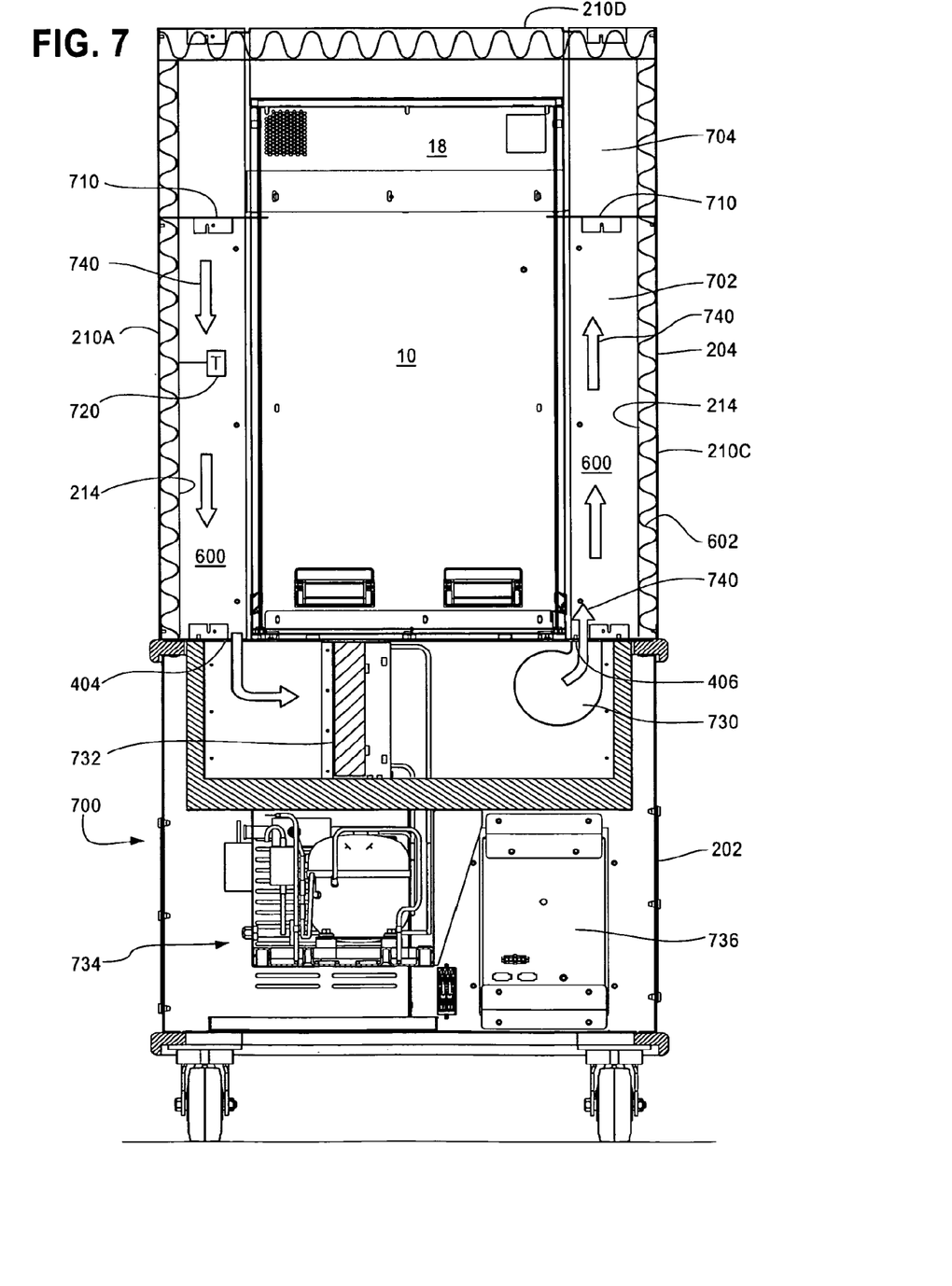
FIG. 7 is a cross-sectional view of the incubation system of FIGS. 2, 3 and 5 taken along the lines 7-7 of FIG. 5, showing the flow path of air circulated in a closed loop between the refrigeration machine in the base and the space between the inner walls of the enclosure and the exterior wall of the incubator.
Figure 8:
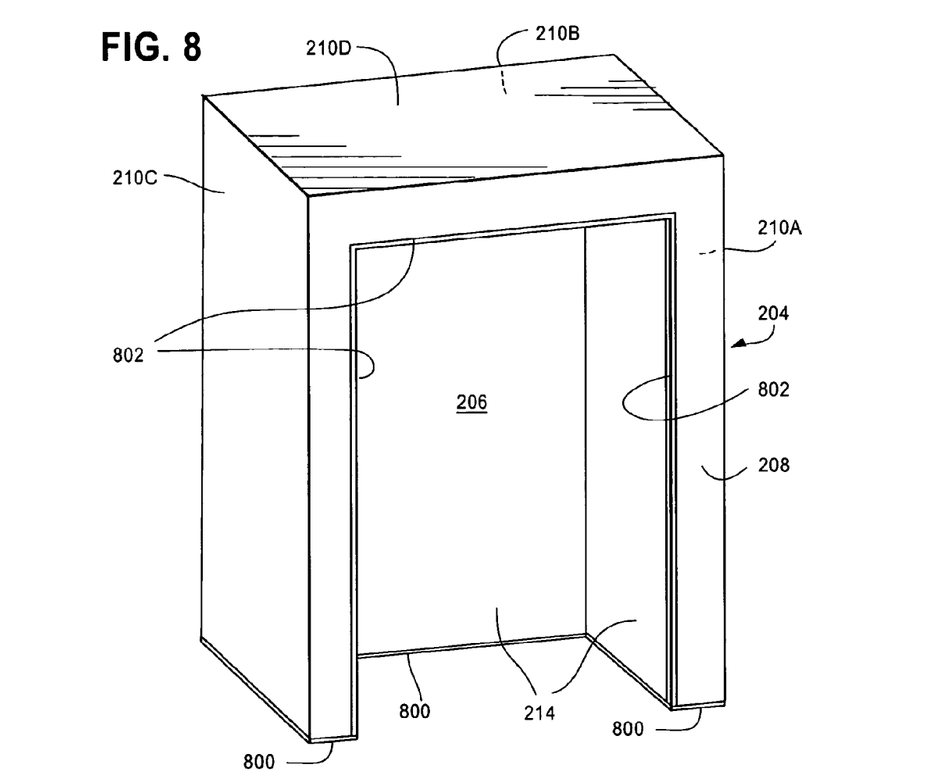
FIG. 8 is a perspective view of the enclosure shown isolated.

In operation, cold air from the refrigeration machine in the base 202 is blown out of the base 202 via holes 406 (FIGS. 4, 6) formed in the top surface 402 of the base 202 into a space or region 600 (FIG. 6, 7) that exists between the exterior surface 410 (FIG. 4) of the incubator 10 and the inner walls 214 (FIGS. 6, 7 and 8) of the enclosure 204. The cold air circulates around the sides and back of the incubator 10 as shown in FIGS. 6 and 7, and back into the base 202 via an air return opening 404 (FIG. 4) in the top 402 of the base 202. The air flows in a closed loop as indicated by the arrows 740 in FIG. 7, thus maintaining a relatively cool immediate ambient environment (e.g., 10-13° C.) for the incubator 10. The entire system of FIG. 2 can be placed in a room temperature environment.

The enclosure 204 includes seals (best shown in FIG. 8 at 800) between the enclosure 204 and the base 202 and seals 802 between the enclosure 204 and the incubator 10 in the location of the void 206. The seals, which may take the form of weather-stripping or similar elastomeric, resilient product, preferably make a substantially air-tight seal between the enclosure 204 and the base 202 and between the enclosure 204 and the incubator 10 in the area of the void 206. The seals 800 and 802 thus prevent ambient air from entering the space or region 600 (best shown in FIGS. 6 and 7) between the enclosure 204 and the incubator 10. This allows for a closed loop air flow system for the refrigeration machine in the base 202 and avoids introduction of humidity and associated condensation issues that might otherwise occur.

The system shown in FIG. 2 allows the incubator 10 to incubate samples at a nominal temperature of 20-25° C., while having the incubation system installed a normal lab environment at room temperature. The use of an external walk-in environmental chamber is not required. The laboratory need not be cooled below room temperature for the incubator 10 to work properly.

Figure 3:
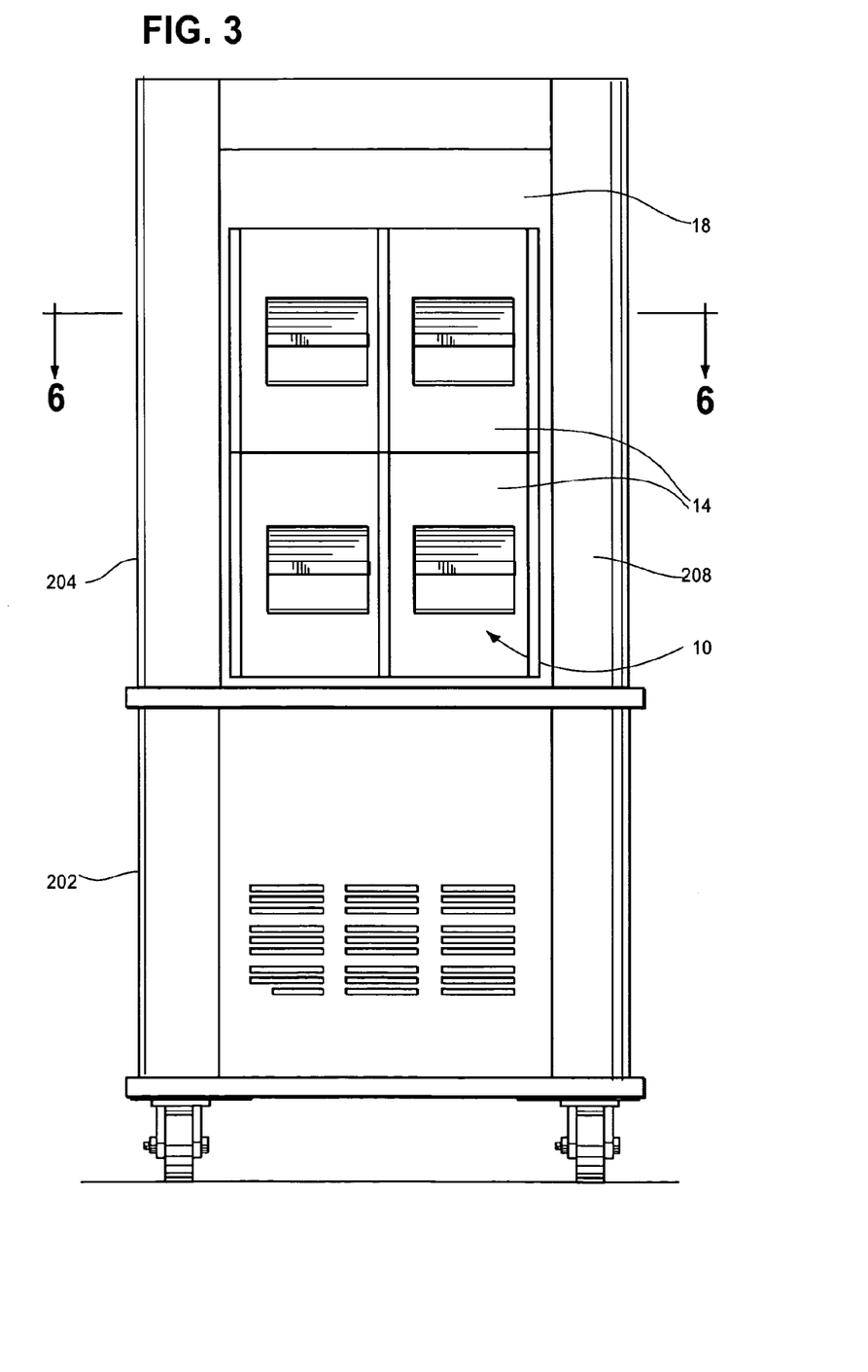
FIG. 3 is a front view of the incubation system of FIG. 2.
Figure 4:
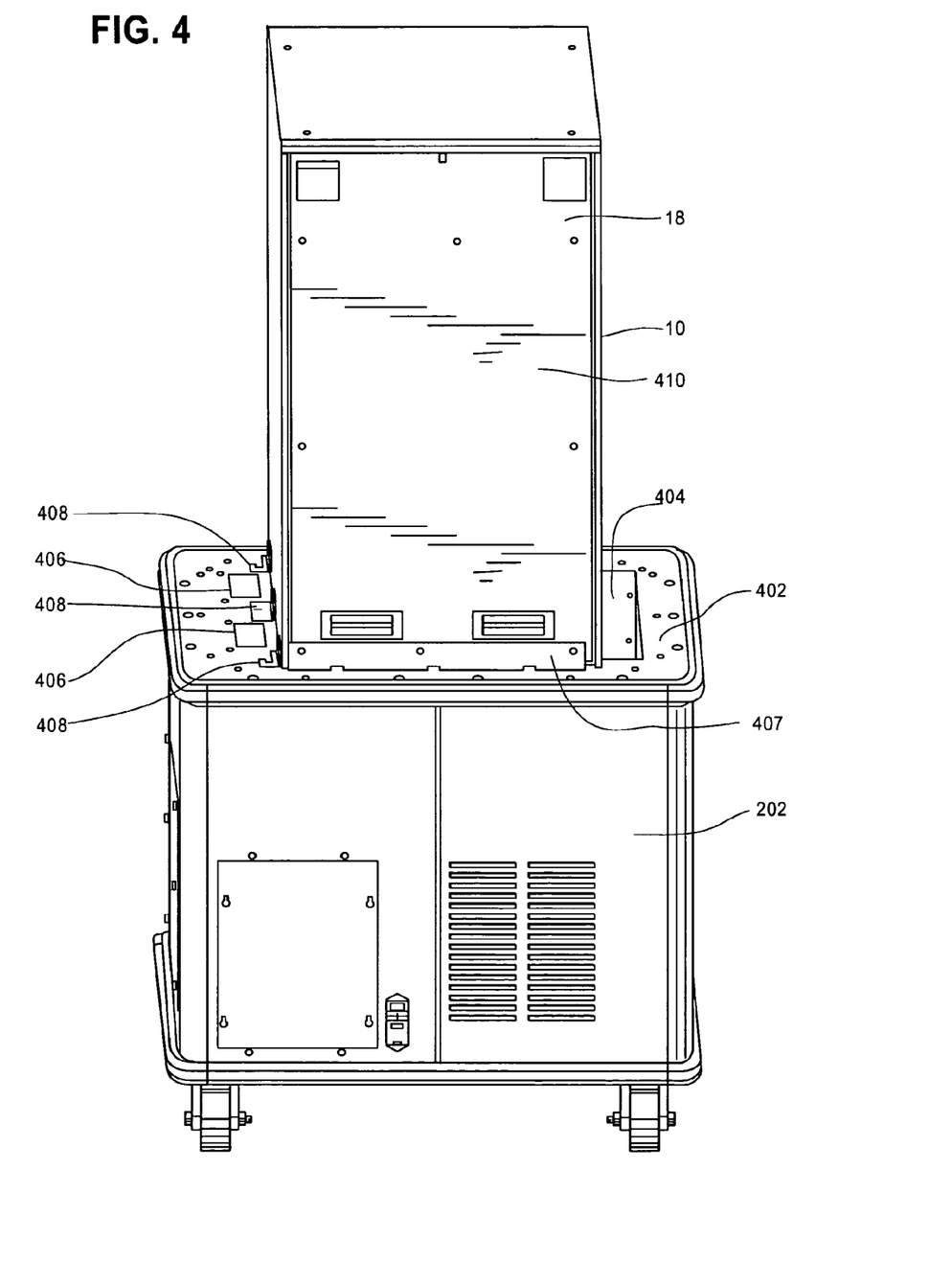
FIG. 4 is a rear view of the incubation system of FIG. 3 but with the enclosure removed, showing the incubator sitting on top of the base and the apertures for egress of cold air from the base and return of air to the base.
Figure 5:
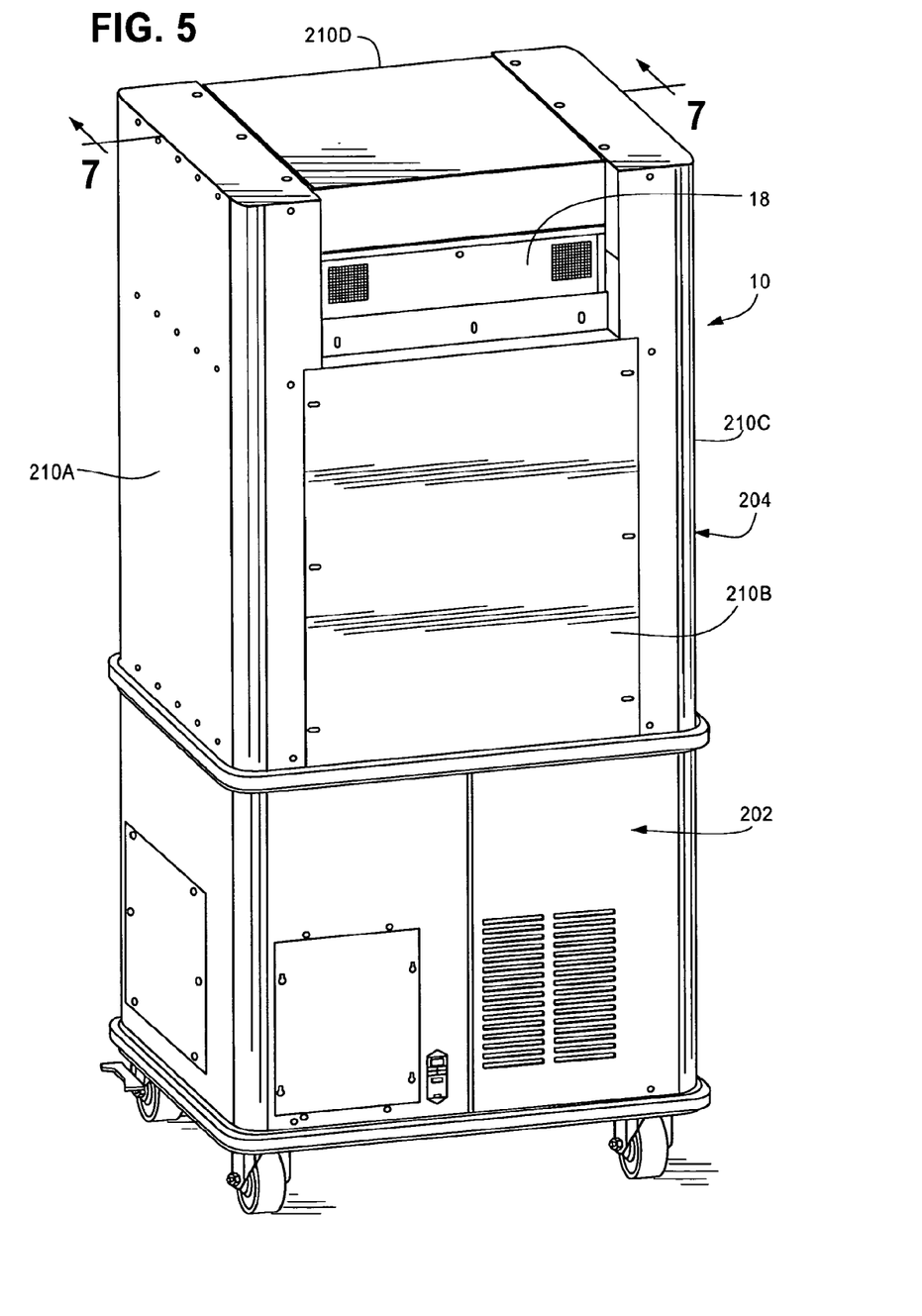
FIG. 5 is a perspective, rear view of the incubation system of FIG. 2 with the enclosure installed on the base and surrounding the incubator.

The enclosure 204 is specifically constructed so as to substantially envelop the incubator 10, as best shown in the FIGS. 2, 3 and 5. The enclosure 204 will typically be constructed with dimensions to fit around and substantially or even completely envelop a particular make and model of incubator, while providing a void or opening in the proper location to thereby expose the access drawers or doors of the incubator 10. As will be seen from FIGS. 6 and 8, the enclosure 204 is oversized relative to the dimensions of the incubator 10, such that a space (600, FIGS. 6 and 7) is defined between the exterior 410 (FIG. 4) of the incubator 10 and the interior walls 214 (FIGS. 6, 7, 8) of the enclosure 204 so as to permit circulation of cold air from the refrigeration machine in this space.

Base 202 (FIGS. 2, 3, 4, 7, 9) and Refrigeration Machine 700

The base 202 in the illustrated embodiment takes the form of a cart or cabinet having wheels as shown in FIG. 2. The base provides a housing or enclosure for the refrigeration machine 700 (FIG. 7) which generates the supply of cold air. With reference to FIG. 4, the base includes a flat top surface 402 which has one or more apertures 406 for egress of cold air from the refrigeration machine and an opening 404 for return of air to the base 202. The incubator is placed on the top surface 402 as shown in FIG. 4 such that the apertures 404 and 406 are positioned external to the periphery of the incubator 10. The incubator 10 is anchored to the top surface 402 by means of brackets 408 connecting the base of the walls of the incubator 10 with the top surface 402. An additional anchor bracket 407 extends across the back of the instrument.

The insulated enclosure 204 is also placed on top of the base 202 as shown in FIGS. 2 and 3. The enclosure 204 is anchored to the top of the incubator and pinned into position with the base 202. The enclosure 204 is positioned on the base 202 such that the inner walls 214 (FIG. 8) of the enclosure 204 are positioned peripheral to the openings 404 and 406 in the top of the base, as shown in FIGS. 6 and 7.

Referring now to FIG. 7, the refrigeration machine 700 includes an evaporator heat exchanger 732 having passages (not shown) for flow of air through the evaporator and one or more fans 730 blowing cold air out of the base 202 into the space 600 between the incubator 10 and the enclosure 202. The refrigeration machine includes conventional refrigeration machinery 734 including a condenser, compressor, and tubing conveying liquid refrigerant to the evaporator 732 and returning gas-phase refrigerant from the evaporator back to the machinery 734. These details are conventional in the refrigeration art. The refrigeration machine 734 may take the form of a standard ice-cream cart refrigeration unit, with the evaporator size or configuration, duty cycle, and/or fans modified to produce temperature at say 10° C., instead of a sub-freezing temperature as would be used in an ice cream application of the refrigeration machine.

FIG. 7 also shows the power supply module 736 which provides power to the refrigeration machine 700. In the event that the incubation system includes a temperature feedback control system, the system will also include a temperature sensor 720 (FIG. 7) placed in the cool chamber space 600 which generates a temperature signal. This signal is provided to a control module contained in the cart 202 (e.g. located in the power supply module 736) which controls the operation of the refrigeration machine 700. Depending on the temperature changes sensed by the sensor 720, the refrigeration machine 700 changes it operational characteristics to either produce cooler or warmer air, or more or less volume of cold air, so as to produce the desired ambient temperature for the incubator 10 in the space 600.

In the illustrated embodiment, the refrigeration machine 700 runs constantly to produce 10° C. air, the enclosure 204 is insulated, and there is no feedback temperature sensor 720. Providing the temperature sensor 720 and a feedback temperature regulation regime may result in a more energy-efficient system.

Incubator 10

The incubator 10 can be any incubator for incubating samples, and the details, form factor, configuration, size, or type of sample incubated is not particularly important. The incubator 10 shown in the drawings, designed for blood collection bottles, is offered by way of example on and not limitation.

Typically, the incubator 10 will have its own electronics module (18 in the drawings), heater and temperature regulation system for controlling the nominal incubation temperature of the incubator. In the embodiment of FIGS. 1-4, the incubator is a box-like structure having an exterior surface 410 defined by vertical walls of a heat conductive material such as sheet metal, but this configuration and choice of materials is not necessary and may vary. Additionally, different types of access devices besides drawers 14 are possible and the particular arrangement of the access device for the incubator is not particularly important. In preferred embodiments, the enclosure 204 is constructed such that it substantially envelops the incubator 10 (as shown in FIGS. 2, 3, 6 and 7) while exposing the access drawers 14 of the incubator 10.

It will be noted in the embodiment of FIGS. 2 and 3 that the front face of the incubator 10 and the drawers 14 are exposed to the ambient conditions (room temperature), while the remaining three sides of the incubator (and the bottom of the incubator) are subject to the cool environment provided by the space 600 of FIGS. 6 and 7 and the relatively cold top surface 402 of the cart 202. Testing has demonstrated that the exposure of the front of the incubator to ambient temperatures is not likely to affect the ability of the incubator to maintain a stable 20-25° C. temperature profile. This is because there is little or no heat transfer from the ambient environment into or out of the interior of the incubator since both the ambient environment and the incubator are maintained at 20-25° C. However, the cool environment present on the sides, back and bottom of the incubator 10 due to cooled space 600 and cold top surface 402 of the cart, and the heat transfer from the walls of the incubator 10 into the air circulating in the space 600 and top of the cart 202, provides a sufficient temperature differential and heat loss from the incubator 10 such that the heating system in the incubator must work steadily to maintain a steady 20-25° C. nominal temperature for the incubator 10. This demand for steady work on the incubator temperature control system allows the incubator temperature control system to reliably maintain the 20-25° C. nominal temperature for the incubator 10.

Enclosure 204

With reference to FIGS. 2, 3, 5, 6, 7, and 8, the enclosure 204 is preferably an insulated structure having a front wall 208, side walls 210A, 210B, 210C and a top panel or wall 210D. The insulation is shown at 602 in FIGS. 6 and 7. The enclosure is shown isolated in a perspective view in FIG. 8. The enclosure 204 has no bottom wall or panel in the illustrated embodiment. The enclosure 204 is fastened to the top of the incubator and pinned into position with the base 202. The enclosure 204 substantially surrounds and envelops the incubator 10. Walls 208, 210A, 210B, and 210C are preferably insulated. For example, 1 to 2 inches of R5 value foam insulation is applied to the shell or skin forming the enclosure 204. The top panel 210D of the enclosure may also be insulated.

Referring to FIG. 7, the enclosure includes baffles 710 that extend inwardly from the walls 214 of the enclosure and which abut the exterior of the incubator 10 immediately below the electronics module 18. The baffles serve to separate the space between the incubator 10 and the enclosure 204 into two compartments, a first compartment 702 below the baffles comprising the cooled space 600 between the incubator and the enclosure 204, and a second compartment 704 located above the baffles and surrounding the electronics module 18 in the incubator. Preferably, cool air from the refrigeration system 700 does not enter the second compartment 704 due to the baffles 710. This prevents condensation from forming in the compartment 704, which could accumulate and lead to problems with the electronics module 18 of the incubator. As shown in the rear view of FIG. 5, there is an opening in the top of the rear side panel 210B to expose the vent openings for the electronics of the incubator and allow the cooling system for the electronics module 18 to operate properly.

The enclosure 204 could be made of a material with intrinsic insulative properties and of sufficient thickness such that additional insulation, e.g., R5 insulation foam, does not need to be added.

Retrofit Kit

In one possible embodiment of this invention, the incubator 10 is a preexisting incubator and the enclosure 204 and base 202 including refrigeration machine 700 (FIG. 7) are provided or sold as a kit 900 (FIG. 9) to the owner of the incubator for the purpose of retrofitting to the preexisting incubator. The enclosure 204 and the base 202 are shipped to the laboratory where the incubator 10 is located, and the base and enclosure are configured as shown in the drawings and described herein to form an incubation system ideally suited for incubation of specimens at room temperature. The enclosure 204 will typically be shipped in a disassembled state and assembled on site by a technician.

Thus, in one possible embodiment of this invention, a method is provided for modifying an incubator. The method includes the steps of a) obtaining a retrofit kit 900 (FIG. 9) comprising (1) a base (202) containing a machine (700, FIG. 7) generating cold air and (2) an insulated enclosure (204) at a site where the incubator 10 is located, the base having a first opening 406 for egress of cold air and a second opening 404 for return of air to the base 202;

b) placing the incubator 10 on the base 202 such that the first opening 406 and the second opening 404 are positioned external to the incubator (see FIG. 4);

c) placing the insulated enclosure 204 on the base 202 (FIGS. 2, 3, 5-7) in a manner such that the insulated enclosure 204 substantially surrounds the incubator 10. The insulated enclosure 204 is sized and shaped so as to define a space (600) between the exterior of the incubator 10 and the enclosure 204. The enclosure 204 is placed on the base 202 such that the first and second openings 406, 404 in the base are positioned within the insulated enclosure in communication with the space 600 (as shown in FIG. 6). Cold air emanates from the base, circulates on the exterior of the incubator, and returns to the base in a closed loop (see FIG. 7). The air flows around the backside of the incubator to the left side where it returns to the refrigeration unit. The air flow within the enclosure 204 flows past the incubator back panel. This cools the back panel, which in turn cools the return air to the incubator heating element. The heating element in the incubator is then forced to turn on in order to maintain the correct incubator temperature.

Optionally, the insulated enclosure includes a void 206 (FIGS. 2, 8) exposing an access feature 14 of the incubator enabling direct access to the contents of the incubator while the incubator is substantially enveloped by the insulated enclosure. As another option, the enclosure 204 completely envelops the incubator 10 and a door (not shown) is provided in the enclosure 204 which is opened to gain access to the access feature 14 of the incubator 10.

In a preferred implementation, the method includes the step of installing seals 800 between the insulated enclosure 202 and the base 202 and seals 802 between the enclosure 204 and the incubator 210 to prevent introduction of ambient air into the space 600 defined between the interior walls 214 of the enclosure 204 and the exterior walls 410 (FIG. 4) of the incubator 10.

Figure 9:
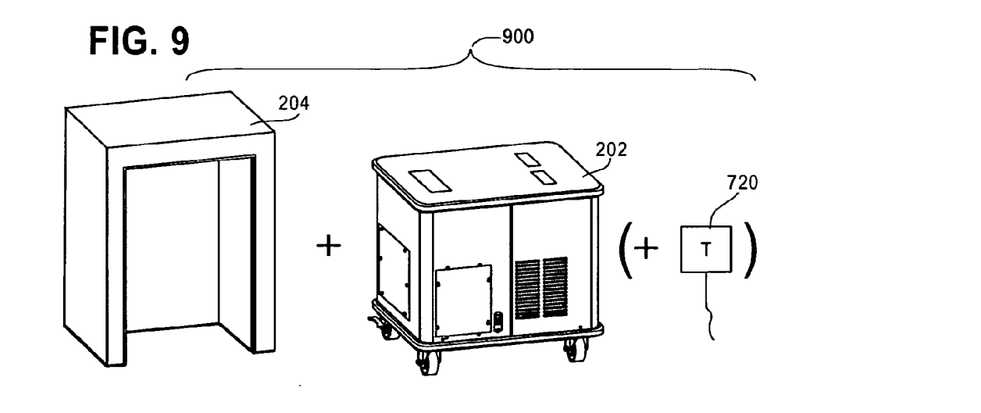
FIG. 9 is an illustration of a retrofit kit that can be furnished to a site such as a laboratory which already has an existing incubator. The kit includes the base and enclosure of FIG. 2, and optionally a temperature sensor for placement in the space between the exterior of the incubator and the interior walls of the enclosure to monitor the temperature in this space. The temperature sensor can be used in a temperature feedback system to regulate operation of the refrigeration machine located in the base.

As shown in FIG. 9, the retrofit kit 900 may also include a temperature sensor 720 which is placed in the space 600 to monitor the temperature in the space. The temperature sensor is placed into electrical communication with a control system for the refrigeration machine 700 to provide for a feedback temperature regulation system.

From the foregoing, it will be appreciated that we have described an incubation system (FIGS. 2-8), comprising in combination:

a) a machine 700 for generating a supply of cold air, b) an incubator 10 having an exterior 410 and an interior and one or more access features 41 on the exterior providing access to the interior of the incubator, the incubator having a system for maintaining the temperature of the interior of the incubator at a nominal desired temperature; and c) an enclosure 204 external from and enveloping the incubator 10 to define a space 600 between the exterior of the incubator and the enclosure (FIGS. 2, 3, 6, 7), wherein the space 600 receives cold air from the refrigeration machine 700 generating the supply of cold air (FIG. 7), and wherein the enclosure 204 is sized and shaped so as to substantially surround the exterior of the incubator, the space 600 defining a region where cold air circulates about the exterior of the incubator (FIGS. 6, 7), and wherein the enclosure further includes a void 206 exposing the one or more access features 14 on the exterior of the incubator 10 wherein a user may directly access contents stored in the incubator while the incubator is enveloped by the insulated enclosure (FIG. 2).

As noted, in a preferred embodiment the incubator temperature control system operates to maintain the interior of the incubator at a nominal desired temperature of between 20 and 25 degrees C. In a preferred embodiment the temperature of the cold air supplied to the enclosure 204 is at least 7° C. cooler than the nominal desired temperature of the incubator.

As shown in FIGS. 2 and 7, the machine for supplying cold air is incorporated into base 202, the enclosure 204 is an insulated enclosure, and enclosure and incubator are placed on the base as shown in FIGS. 4 and 5, and wherein the base and the insulated enclosure are constructed and arranged as a retrofit assembly or kit (FIG. 9) for a pre-existing incubator.

It will be noted that in the illustrated embodiment the source of the cold air is a refrigeration system in the base 202. This is not essential, and the refrigeration system could be located to the side, back or above the incubator, or even remotely and cold air ducted into the space 600 between the enclosure and the incubator, e.g., in the situation where there are multiple incubators and a single, common refrigeration system supplies cold air to each incubator and associated enclosure. Thus, the invention can also be characterized as an incubation apparatus made up of (a) an incubator 10, the incubator having an exterior and an interior and one or more access features on the exterior providing access to the interior of the incubator, the incubator further comprising a source of heat for maintaining the interior of the incubator at a nominal temperature; and (b) an insulated enclosure 204 enveloping the incubator, the enclosure having an interior space or region 600 receiving cold air from a source (which may or not be located in a base for the incubator), wherein the insulated enclosure is sized and shaped so as to substantially surround the exterior of the incubator, the interior space defining a region wherein air from the source at a temperature below the nominal temperature may circulate over the exterior of the incubator.

In preferred embodiments, the incubator 10 incubates sample containers containing samples collected from human patients, e.g., blood. Preferably, the incubator further includes a sensor for obtaining sensor readings from the sample containers, and wherein the nominal temperature of the incubator is in the range of between 20-25° C. An example of the sensor for blood collection bottles is described in U.S. Pat. No. 5,164,796, which is incorporated by reference herein. Other sensors are known in the art and may be interchanged with the sensor of the '796 patent.

In still another form of the invention, the invention can be characterized as a cool chamber apparatus for installation around an incubator 10, the incubator having a front side (shown in FIGS. 1, 2, and 3) and one or more access features 14 of obtaining access to the interior of the incubator placed on the front side of the incubator, the cool chamber apparatus comprising: an insulated enclosure 204 specifically sized and shaped so as to substantially envelop the incubator 10 and having a top panel 210D and first, second and third side panels (210A, B, C) for covering the first, second and third side panels of the incubator and a fourth side 208 having an opening 206, wherein the opening in the enclosure 204 exposes the access features of the incubator.

Further Configurations

A further variation on the disclosed embodiments is contemplated in which the enclosure 204 is not provided with any insulation per se. In this embodiment, there is a feedback system in the form of a temperature sensor 720 (FIG. 7) that monitors the air temperature in the space 600 between the enclosure 202 and the incubator 10. The temperature sensor sends a temperature signal to the source of cold air (machine 700) and the source is regulated (e.g., to blow air with greater or lesser velocity or to generate colder or warmer air) to maintain a certain desired temperature (e.g., 10° C.) in the space between the enclosure and the incubator as ambient conditions outside of the enclosure change.

As a variation on this approach, the enclosure is insulated (as in the illustrated preferred embodiment), but a temperature sensor is placed in the space between the enclosure and the incubator, and the source of cold air is regulated to maintain the temperature in the space between the enclosure and the incubator to a desired temperature. This approach may result in a system which has maximum energy efficiency, but may be a more costly implementation.

Thus, in an alternative embodiment, an incubation system is contemplated, comprising in combination:

a) a machine 700 for generating a supply of cold air;

b) an incubator 10 having an exterior and an interior and one or more access features on the exterior providing access to the interior of the incubator, the incubator having a system for maintaining the temperature of the interior of the incubator at a nominal desired temperature;

c) an enclosure 204 external from and substantially enveloping the incubator to define a space 600 between the exterior of the incubator and the insulated enclosure, wherein the space receives cold air from the machine 700 generating the supply of cold air; and d) a temperature sensor 720 monitoring the temperature in the space 600 between the exterior of the incubator 10 and the enclosure 204 and generating a temperature signal;

wherein the machine 700 operates to regulate the temperature in the space 600 between the exterior of the incubator and the insulated enclosure to a desired set point lower than the nominal desired temperature of the incubator in response to the temperature signal from the temperature sensor.

In one embodiment, the enclosure 204 is substantially uninsulated, i.e., having no additional insulation added and made from material which does not have a substantial intrinsic insulation property, such as plain sheet metal. Alternatively, the enclosure is insulated as shown in FIGS. 6 and 7.

A further method of modifying an incubator 10 is also contemplated, comprising the steps of:

a) obtaining a retrofit kit 900 (FIG. 9) at a site where the incubator 10 is located, the retrofit kit comprising (1) a base 202 containing a machine generating cold air, and (2) an enclosure 204 for the incubator, and (3) a temperature sensor 720, the base 202 having a first opening for egress of cold air and a second opening for return of air to the base;

b) placing the incubator on the base (FIG. 4);

c) placing the insulated enclosure on the base in a manner such that the insulated enclosure surrounds the incubator and defines a space between the exterior of the incubator and the incubator, the insulated enclosure placed on the base such that the first and second openings in the base are peripheral to the incubator and are in communication with the space such that cold air may emanate from the base, circulate on the exterior of the incubator, and return to the base in a closed loop (FIGS. 5-7); and d) placing the temperature sensor 720 in the space 600 between the enclosure and the incubator and communicatively coupling the temperature sensor and the machine generating the cold air (FIG. 7).

Variation from the physical configuration or form factor of the insulated enclosure and cart from that shown in the drawings is possible and indeed likely, and such variation is considered to be within the scope of the invention. The specific embodiment of the enclosure 204 that has been disclosed was designed for a particular incubator 10 (a commercial product of the applicants' assignee), but for different sizes or shapes of incubators the size and shape of the insulated enclosure (and the base) will of course be different. Thus, the embodiments that are disclosed in particularity are offered by way of example and not limitation. Persons skilled in the art will be readily able to adapt the teachings of this document regarding the source of cold air, the cart or base and the enclosure to suit different incubators and such variations are considered within the scope of this invention.

In the appended claims, the term "insulated enclosure" is intended to encompass (a) an enclosure which has a skin or surface of a material which does not have substantial insulation properties but which has insulation specifically added to it (e.g., foam), as well as (b) an enclosure which is made from a material and/or thickness such that it has substantial intrinsic insulation characteristics but does not have any additional insulation material added to it, or (c) a combination of (a) and (b). Additionally, the term "cold air" is intended to refer to air which has been cooled, e.g., by a refrigeration unit. Such air will typically be a temperature that is below the nominal temperature of the incubator, such as 10° C.

These and still other variations from the particular embodiments disclosed are intended to be encompassed by the invention. All questions concerning scope of the invention are to be answered by reference to the appended claims.

The invention claimed is:

1. A method of modifying a stand-alone, self-contained incubator, the method comprising the steps of:

a) obtaining a kit comprising:

an incubator having a heating element for maintaining the interior temperature of the incubator within a temperature range of 20-25° C. and an electronics module for controlling the heating element in a top portion of the incubator, an insulated enclosure having a first compartment surrounding the incubator and a second compartment surrounding the top portion of the incubator, the first compartment and the second compartment being separated from each other using a baffle in contact with the incubator;

a base containing a machine generating a supply of cold air, the base having a first opening for egress of cold air and a second opening for return of air to the base into the first compartment, b) placing the incubator on the base such that the first opening and the second opening are positioned external to the incubator;

c) placing the insulated enclosure on the base in a manner such that the insulated enclosure substantially surrounds the incubator, the insulated enclosure constructed so as to define a space between the exterior of the incubator and the enclosure, the insulated enclosure placed on the base such that the first and second openings in the base are positioned within the insulated enclosure in communication with the space such that cold air may emanate from the base, circulate on the exterior of the incubator within the first compartment, and return to the base in a closed loop.

2. The method of claim 1, wherein the method further comprises:
   d) installing seals between the insulated enclosure and the base and between the insulated enclosure and the incubator to prevent introduction of ambient air into the space between the interior of the insulated enclosure and the exterior of the incubator.

3. A method of modifying a stand-alone, self-contained incubator, the method comprising the steps of:
   a) obtaining a kit at a site where the incubator is located, the kit comprising (1) a base containing a machine generating cold air, (2) an enclosure having a first compartment surrounding the incubator and a second compartment surrounding an electronics module in a top portion of the incubator, the first compartment and the second compartment being separated from each other using a baffle in contact with the incubator, and (3) a temperature sensor, the base having a first opening for egress of cold air and a second opening for return of air to the base;
   b) placing the incubator on the base, wherein the stand-alone, self-contained incubator has an exterior and an interior and one or more access features on the exterior providing access to the interior of the incubator, the incubator having a heating element for maintaining the temperature of the interior of the incubator at a nominal incubation temperature;
   c) placing the enclosure on the base in a manner such that the enclosure surrounds the incubator and defines a space between the exterior of the incubator and the enclosure, the enclosure placed on the base such that the first and second openings in the base are peripheral to the incubator and are in communication with the space such that cold air may emanate from the base, circulate on the exterior of the incubator, and return to the base in a closed loop; and
   d) placing the temperature sensor in the space between the enclosure and the incubator and communicatively coupling the temperature sensor and the machine generating the cold air so as to permit temperature feedback regulation of the operation of the machine generating the cold air.

4. The method of claim 3, wherein the method further comprises:
   e) installing seals between the enclosure and the base and between the enclosure and the incubator to prevent introduction of ambient air into the space between the interior of the enclosure and the exterior of the incubator.

5. The method of claim 3, wherein the enclosure is an insulated enclosure.

* * * * *